United States Patent
Gollier et al.

(10) Patent No.: US 10,321,820 B1
(45) Date of Patent: Jun. 18, 2019

(54) MEASURING OPTICAL PROPERTIES OF AN EYEWEAR DEVICE

(71) Applicant: Facebook Technologies, LLC, Menlo Park, CA (US)

(72) Inventors: Jacques Gollier, Redmond, WA (US); Yusufu Njoni Bamaxam Sulai, Bothell, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 15/850,815

(22) Filed: Dec. 21, 2017

(51) Int. Cl.
  *A61B 3/103* (2006.01)
  *A61B 3/107* (2006.01)
  *G02F 1/29* (2006.01)
  *G02B 27/01* (2006.01)
  *G02B 6/26* (2006.01)

(52) U.S. Cl.
  CPC ............. *A61B 3/103* (2013.01); *A61B 3/107* (2013.01); *G02B 6/264* (2013.01); *G02B 27/017* (2013.01); *G02F 1/29* (2013.01)

(58) Field of Classification Search
  CPC ..... A61B 3/0025; A61B 3/103; A61B 3/1015; A61B 3/14; A61B 3/10
  USPC .......................................................... 351/205
  See application file for complete search history.

(56) References Cited

U.S. PATENT DOCUMENTS

| | | | | |
|---|---|---|---|---|
| 2003/0210378 | A1* | 11/2003 | Riza | A61B 3/066 351/205 |
| 2010/0292999 | A1* | 11/2010 | Verma | A61B 3/005 705/2 |
| 2016/0166140 | A1* | 6/2016 | Lawrenson | A61B 3/0025 351/208 |

* cited by examiner

*Primary Examiner* — Mohammed A Hasan
(74) *Attorney, Agent, or Firm* — Fenwick & West LLP (57) ABSTRACT

A user device comprises an imaging device and a controller. The imaging device captures one or more images of a test pattern presented by a display surface through a lens of eyewear device and the test pattern not through the lens in accordance with imagining instructions from the controller. The controller generates imaging instructions and provides the imaging instructions to the imaging device. The controller determines one or more optical parameters of the eyewear device based on the captured one or more images of the test pattern as seen through the lens and the test pattern not seen through the lens. The optical parameters may include an optical power of the lens or an inter-pupillary distance of the eyewear device.

20 Claims, 9 Drawing Sheets

MEASURING OPTICAL PROPERTIES OF AN EYEWEAR DEVICE

BACKGROUND

This disclosure relates generally to determining optical properties of a corrective lens for a user, and specifically to determining optical properties of an eyewear device.

In an artificial reality systems, one problem to take into consideration is that a large portion of the population wear corrective lenses to correct their vision (e.g., to correct for myopia, hyperopia, astigmatism, etc.). A solution to this problem is a head-mounted display (HMD) with a mechanical design to allow users to wear their correction lenses (e.g., glasses) inside their HMD. However, such an HMD would be larger in volume to accommodate for the glasses inside the HMD and may be uncomfortable to the user. Also, such a configuration adds complexity for implementing functions such as eye tracking and face tracking. Another solution is an HMD that includes a focus mechanism to allow the user to adjust a position of a lens in an HMD. However, while this solution enables correction of myopia and hyperopia, it does not enable correction for astigmatism. Additionally, it is possible for users to make adjustments that are not precise that would negatively impact their user experience with the HMD. A third solution is an HMD that includes corrective lenses to allow users to wear an HMD without needing to wear their own eyewear device (e.g., eyeglasses). These corrective lenses may be a corrective insert that can be placed in or removed from an HMD to customize the viewing experience to a user. While this solution may increase user comfort and provide correct adjustment for user vision, a user may not know how to select an appropriate corrective insert to customize their own viewing experience.

SUMMARY

An application operating on a user device (e.g., smartphone, tablet, etc.) or on a server enables a user that typically wears an eyewear device to select an appropriate corrective insert and/or spacing of the corrective insert for an HMD. The HMD may be part of an artificial reality system. The application instructs the user to place an eyewear device in between a secondary device that includes an electronic display (e.g., desktop computer, laptop, tablet, television, etc.) displaying a test pattern and an imaging device of the user device. An imaging device (e.g., camera of smartphone, tablet, etc.) of the user device captures one or more images of the test pattern through the one or both prescription lenses of the eyewear device and the test pattern not through any lens of the eyewear device. The application determines one or more optical parameters (e.g., optical power, inter-pupillary distance, etc.) of the eyewear device based on one or more captured images.

In one embodiment, the user device comprises an imaging device and a controller. The controller generates imaging instructions and provides the imaging instructions to the imaging device. The imaging device captures images of a test pattern presented by a display surface through one or both lenses of eyewear device and the test pattern not through any lens of the eyewear device in accordance with imagining instructions from the controller. The display surface may be a surface with a test pattern printed on it. The display surface may be a surface of an electronic display that displays the test pattern. Additionally, the controller may communicate display instructions to the electronic display to display the test pattern. The controller determines one or more optical parameters of the eyewear device based on the captured one or more images. The optical parameters of the eyewear device may include an optical power of the lens or an inter-pupillary distance (IPD) of the eyewear device, the IPD is a distance between centers of the pupils of eyes of a user of the eyewear device.

BRIEF DESCRIPTION OF THE DRAWINGS

Figure (FIG. 1 is a system environment for determining one or more optical parameters of an eyewear device, in accordance with one or more embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Disclosed is a system for determining one or more optical parameters of an eyewear device with a user device such as a tablet or smartphone and a secondary device (e.g., electronic display of a laptop, desktop, etc.). The user device includes an imaging device and a controller. The imaging device captures images through a lens of an eyewear device of a test pattern presented by a display surface in accordance with imagining instructions. The display surface is a surface that displays the test pattern. The display surface may be a surface with test pattern printed on it or a surface of an electronic display that displays the test pattern. The controller generates imaging instructions and provides the imaging instructions to the imaging device. The controller also determines one or more optical parameters of the eyewear device based on the captured one or more images of the test pattern (as seen through the lens and the test pattern as not seen through the lens). The optical parameters of the eyewear device may include an optical power of the lens or an IPD. An optical parameter is a characteristic of the eyewear device 132 relating to sight. An optical parameter may be an IPD, optical power of a lens, axis of a lens, add of a lens of a lens or any combination thereof. The optical power of the lens 130 may be for a spherical or cylindrical correction. For a cylindrical correction, the optical parameter includes an axis of the lens which indicates how the cylindrical power in the lens is positioned (e.g., 90 degrees for vertical and 180 degrees for horizontal). For multifocal eyewear devices, the optical parameter includes an add of the lens which describes added magnifying power applied to a region of the multifocal lenses (e.g., bifocal lenses). Thus, a user of an HMD who normally wears prescription glasses can select an appropriate corrective insert for the HMD using the determined optical parameter of the eyewear device to wear the HMD without their prescription glasses. Also, for a user of an HMD that includes adjustment capabilities to correct for a user's vision, the user can select an adjustment using the determined optical parameter of the eyewear device. For example, the HMD may include an adjustment knob (i.e., focus mechanism) with some labeled gradations to adjust a position of a lens in an HMD. Thus, the user can make appropriate adjustments corresponding to the determined optical parameter to improve their user experience with the HMD.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

System Architecture

Figure 1:
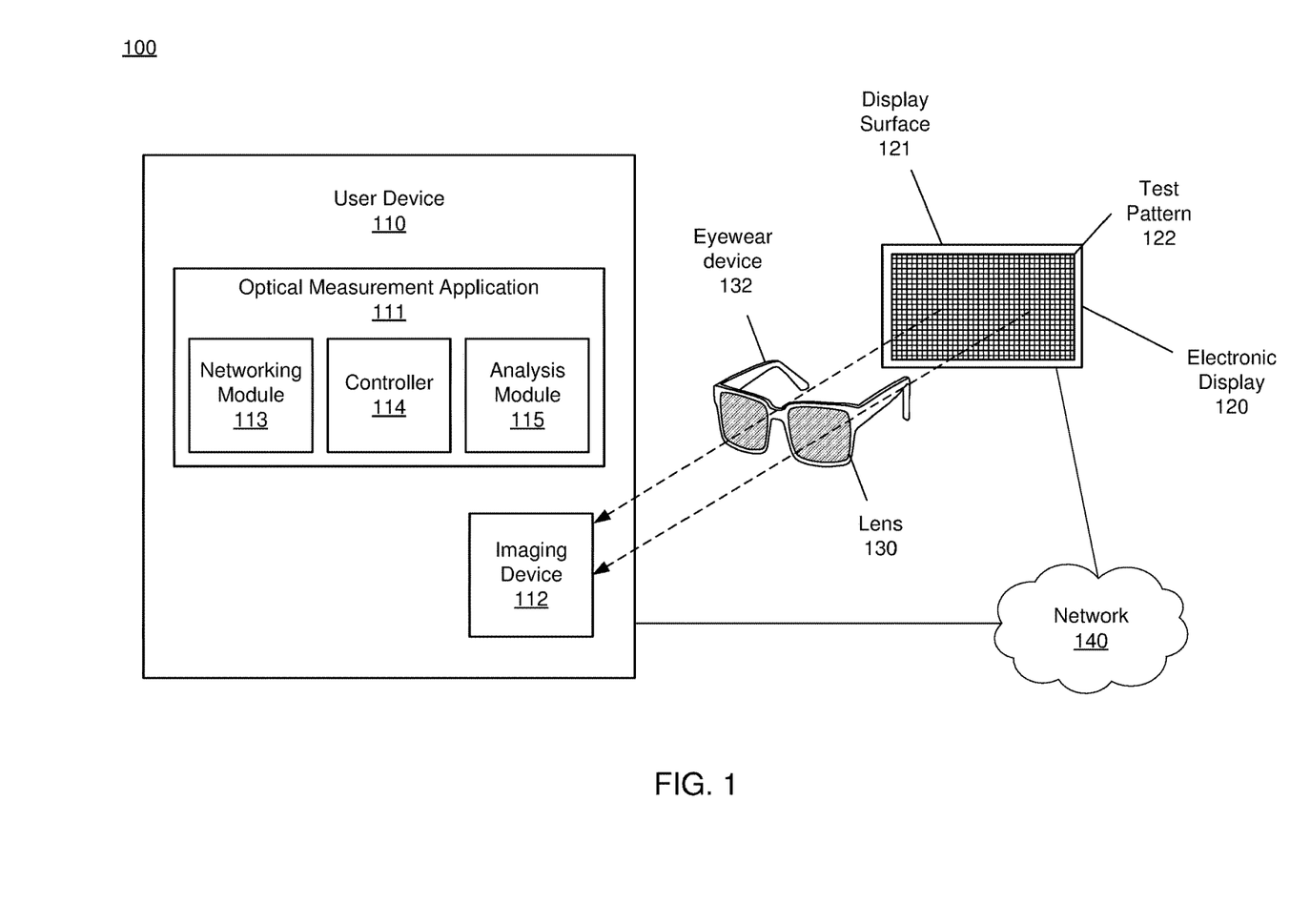

FIG. 1 is a system environment 100 for determining one or more optical parameters of an eyewear device 132, in accordance with one or more embodiments. The system environment 100 includes a user device 110, an optional network 140, and an optional electronic display 120. In other embodiments, the system environment 100 comprises additional or fewer devices than those described herein. For example, the system environment 100 may include just the user device 110. Similarly, the functions can be distributed among different entities in a different manner than is described here.

The network 140 provides a communication infrastructure between the user device 110 and the electronic display 120. The network 140 is typically the Internet, but may be any network, including but not limited to a Local Area Network (LAN), a Metropolitan Area Network (MAN), a Wide Area Network (WAN), a mobile wired or wireless network (e.g., BLUETOOTH, WiFi), a private network, a virtual private network, or some combination thereof. In one embodiment, the network 140 uses standard communications technologies and/or protocols. In another embodiment, the entities can use custom and/or dedicated data communications technologies.

The electronic display 120 presents images in accordance with display instructions. The electronic display 120 receives display instructions via the network 140 from the user device 110 or from a remote server (not shown). The display instructions can be sent directly to the electronic display 120 via the user device 110. Alternatively, a controller 114 of the user device 110 can ping a remote server to generate and provide display instructions to the electronic display 120. The display instructions include a test pattern 122 for the electronic display 120 to display. The electronic display 120 can be a display of a laptop, a desktop, a smart television, an electronic billboard. Examples of the electronic display 120 include: a liquid crystal display (LCD), an organic light emitting diode (OLED) display, an active matrix organic light-emitting diode display (AMOLED), some other display, or some combination thereof. The display surface 121 is a surface that displays the test pattern 122. In this embodiment, the display surface 121 is a surface of the electronic display 120 that displays the test pattern 122. In other embodiments, the system 100 may not include an electronic display 120 and the display surface 121 may be a surface with a test pattern 122 printed on it. For example, the display surface may be a surface of a piece of paper that the test pattern 122 is printed on.

The eyewear device 132 is a device that is worn on the face of a user to correct for deficiencies of the eyesight of a user. The eyewear device 132 is a device that includes at least one lens 130 and may include a lens 130 for each eye of the user. The eyewear device 132 may include a frame. In one embodiment, the eyewear device 132 is prescription glasses. In another embodiment, the eyewear device 132 can be a near eye display for an artificial reality head set. In an alternative embodiment, there may be no frame of the eyewear device 132 and just a lens 130.

The user device 110 is a device with imaging and in some embodiments networking capability. The user device 110 includes an optical measurement application 111 and an imaging device 112. The optical measurement application 111 interfaces with the imaging device 112 and in some embodiments the electronic display 120 to determine one or more optical parameters of the eyewear device 132. The optical measurement application 111 includes a controller 114, and an analysis module 115. In some embodiments, the optical measurement application 111 may also include a networking module 113. In one embodiment some of these entities are software application modules executing on the user device 110. For example, the networking module 113, the controller 114, and the analysis module 115 may be integrated into an application executing on a smart phone. The user device 110 may be, e.g., a mobile phone, a tablet, a smart camera, a laptop with a processor and a camera, or some combination thereof. In other embodiments, the user device 110 is a device with imaging capability and does not have networking capability.

The imaging device 112 is a device that captures images. The imaging device 112 may be a camera on a mobile phone, tablet, or laptop. The imaging device 112 may be a smart camera. The imaging device 112 may include control parameters to set conditions for capturing images. The control parameters may include an enable, a video enable, an exposure, a time delay, and an image dimension parameter.

An enable parameter can start or stop capture of an image. The video enable parameter starts or stops capture of a series of images spaced apart at regular time intervals. The exposure parameter sets the length of exposure time for capturing an image. The time delay parameter starts sets a time delay before a start of capturing an image. The image dimension sets the image dimension (e.g., aspect ratio) and/or image resolution for capturing an image.

The networking module 113 determines a communication pathway to the electronic display 120. The networking module 113 establishes the communication pathway to the electronic display 120 through the network 140. For example, the networking module 113 establishes communication to the electronic display 120 through the Internet. In another example, the networking module 113 establishes a peer-to-peer connection (e.g., BLUETOOTH) between the user device 110 and the electronic display 120.

The controller 114 generates imaging instructions and provides the imaging instructions to the imaging device 112. The controller 114 may communicate or provide display instructions to the electronic display 120.

Display instructions include instructions for an electronic display 120 to display a test pattern 122. In one embodiment, the controller 114 provides the test pattern 122 to the electronic display 120 through the network 140. In another embodiment, the controller 114 directly provides the test pattern 122 to the electronic display 120 through the network 140. Alternatively, the controller 114 may provide a link to the electronic display 120 and the electronic display 120 may download the test pattern through the link via an external server through the network 140. In another embodiment, the controller 114 may indirectly provide the display instructions to the electronic display 120. For example, the controller 114 may ping a remote server to provide the display instructions to the electronic display 120. The test pattern 122 is image data that is configured to produce measurable features when a Fourier Transform is applied to the image data. An example of the test pattern 122 is shown as a reference image (e.g., portion of the captured image that is not through a lens of the eyewear device) in FIGS. 3A and 3B as a pattern of grid lines with known spacing. In one embodiment, a user may provide the test pattern 122 or instructions for obtaining the test pattern 122 to the electronic display 120 responsive instructions provided to the user via the user device 110.

The imaging instructions include instructions for an imaging device 112 to capture one or more images through an eyewear device 132 of a test pattern 122 presented by a display surface 121. The imaging instructions may include instructions for the imaging device to capture the one or more images responsive to a user input. For example, the imaging instructions may include instructions to a user which are performed before or during capture of images of the imaging device 112. The instructions to the user may include placing the eyewear device 132 at a specific distance between the display surface 121 and the imaging device 112. For example, the instructions to the user may be to place the eyewear device 132 a first distance from the display surface 121 and place the imaging device 112 a second distance from the eyewear device 132. The instructions to the user may also include moving the imaging device 112 along an axis connecting the surface of the imaging device 112 and the display surface 121 (e.g., as shown by one of the dotted lines in FIG. 1). For example, the instructions to the user may include instructions to move the imaging device 112 relative to the eyewear device 132 to change the spacing between the imaging device and the eyewear device 132.

The instructions to the user may also include moving the eyewear device 132 relative to the imaging device 112 and display surface 121 to change the distance of the eyewear device 132 to the imaging device 112 and the display surface 121 while keeping the overall distance of the imaging device 112 to the display surface 121 constant. In one or more embodiments, the controller 114 instructs the imaging device 112 to capture an image responsive to the test pattern 122 or features of the test pattern 122 being in a field of view of the imaging device 112, being in focus, having acceptable lighting conditions, or any combination thereof. In an alternative embodiment, the controller 114 instructs the user to activate the imaging device 112 to capture the image of the test pattern 122 through the prescription lens. In one embodiment, the controller 114 instructs the imaging device 112 to capture a video comprising a plurality of images at different times. For example, the imaging device 112 may capture a video while the user is moving the eyewear device 132 to change the spacing between the imaging device and the eyewear device 132.

Figure 3A:
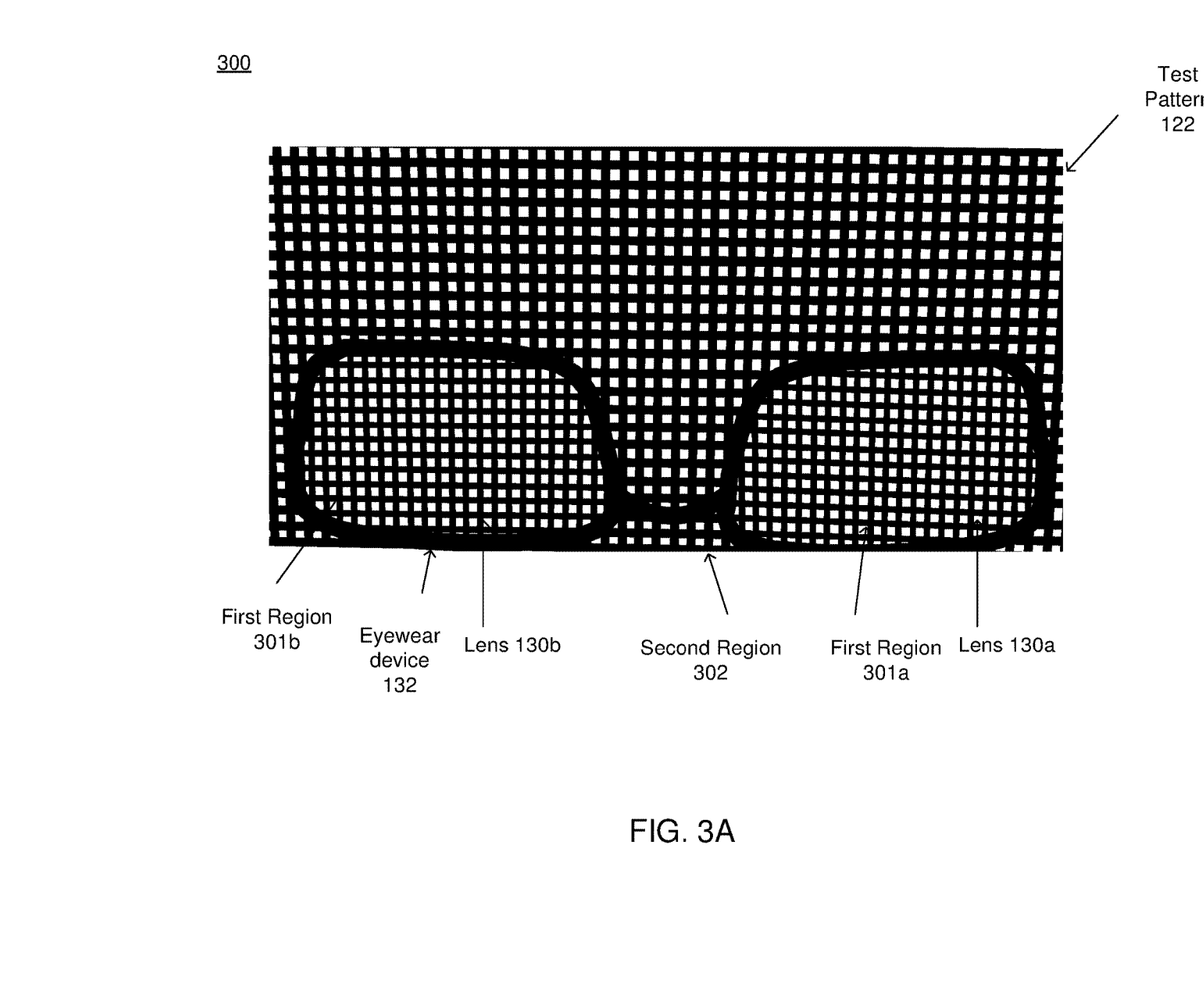
FIG. 3A is an example test image that includes an eyewear device, in accordance with one or more embodiments.
Figure 3B:
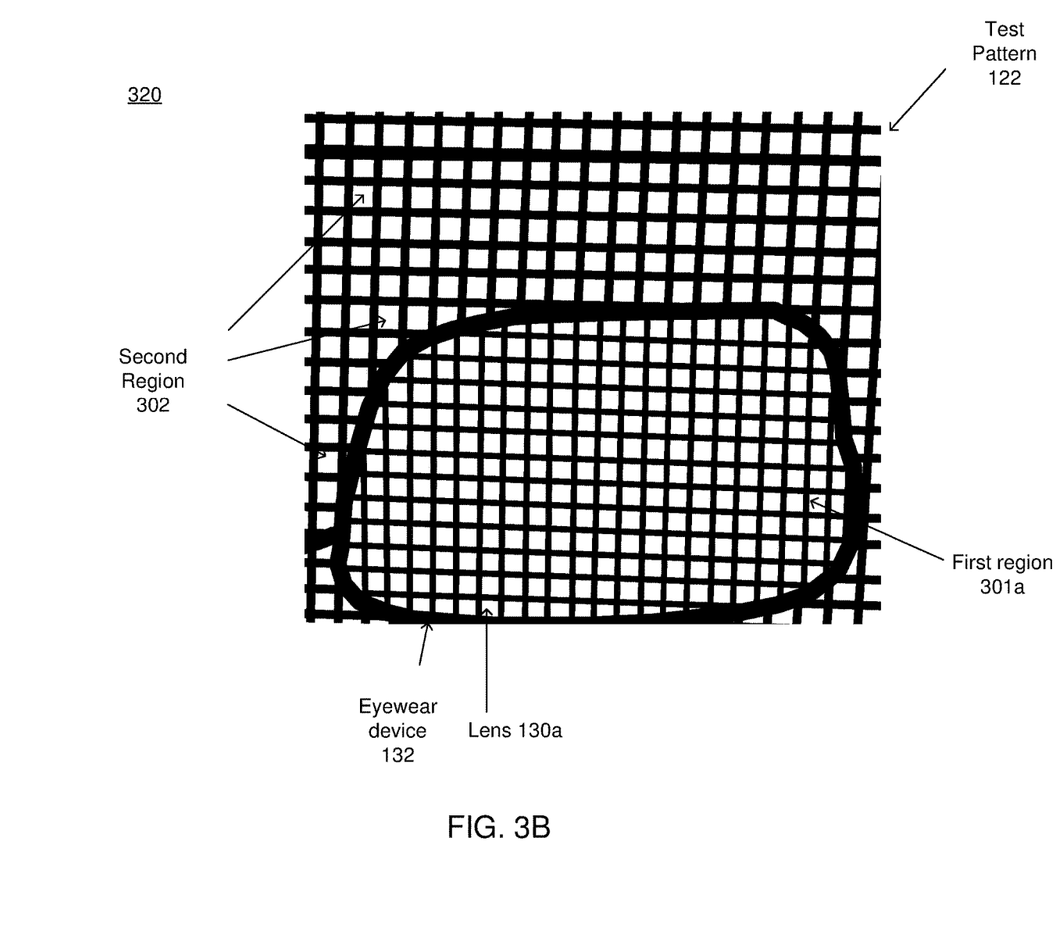
FIG. 3B is a portion of the test image that includes a lens of the eyewear device of FIG. 3A, in accordance with one or more embodiments.
Figure 3C:
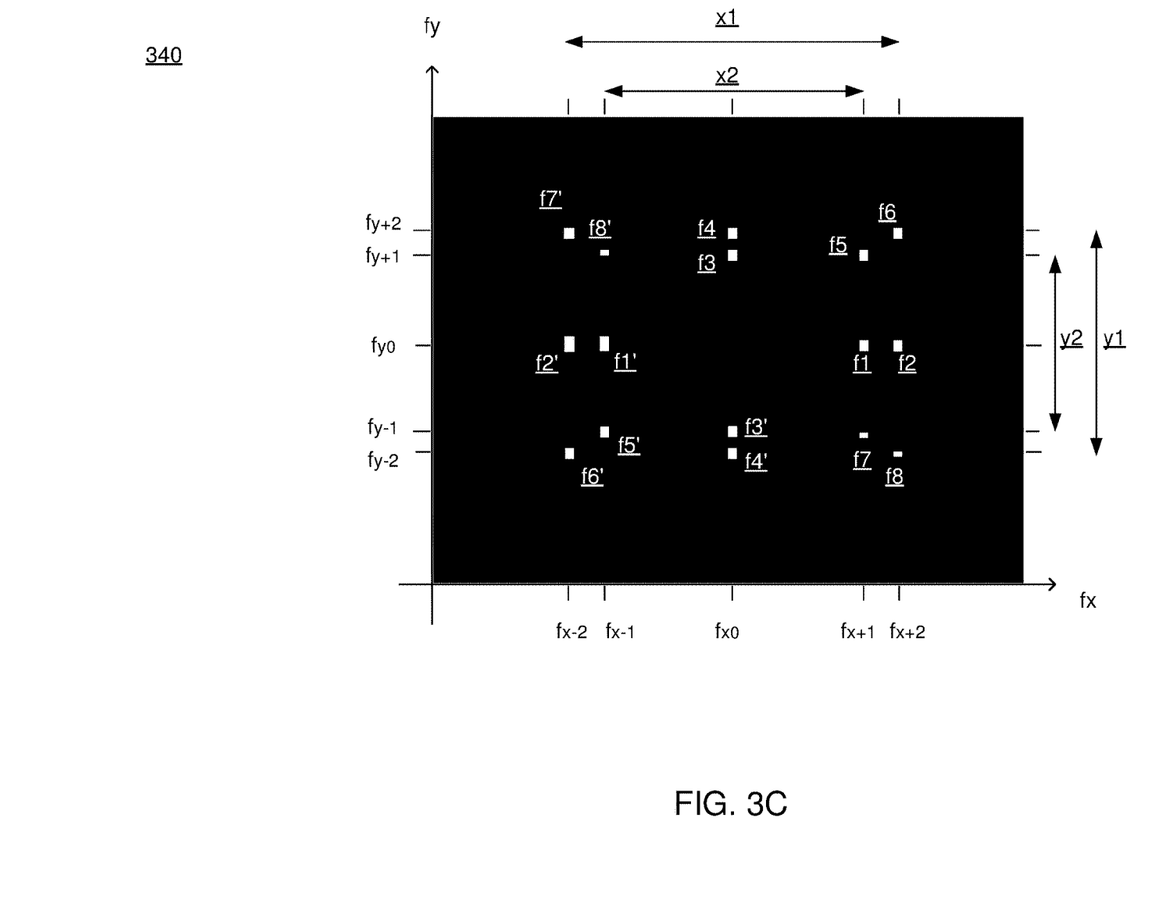
FIG. 3C is an example Fourier Transform of a region of the portion of the test image that includes the lens of the eyewear device of FIG. 3B, in accordance with one or more embodiments.

The purpose of acquiring the image like the one shown on FIG. 3B is to determine the image magnification factor M that is created by the correction lens. By measuring the pitch of the grid (i.e., the test pattern) as seen through the lens and measuring the pitch of the grid as seen without the lens, one can determine the magnification factor M as the ratio between both. Note that different types of test patterns can be used to make the magnification determination. As an example, FIG. 3B shows the case where the test pattern is a square grid. However, the test pattern could also be any set of features (e.g., dots, squares, etc.) put on a periodic grid. Also, there are different ways of determining the pitch. One way includes calculating the Fourier transform of the test pattern in the captured image. Since the test pattern is made of a periodic pattern, its Fourier transform will present a series of peaks and the position of the peaks is representative of the image frequency content which is equal to the inverse of the pitch. As an example, FIG. 3C shows the Fourier transform of FIG. 3B. Since FIG. 3B includes both the test patterns (as seen through the lens and not seen through the lens), the Fourier transform in FIG. 3C includes peaks corresponding to both parts of the image. Other algorithms are also possible such as detecting the position of the image features (e.g., lines, dots, squares, etc.) to get the information of the pitch by calculating the distance between the features.

In one embodiment, the imaging instructions may include instructions for a user to place the imaging device 112 a specific distance away from the display surface 121 without the lens 130 in between for purposes of capturing one or more calibration images. A calibration image may be used as a reference image during analysis of captured images. In other embodiments, different portions of a captured image is used during analysis of the captured image and no separate calibration image is used.

The analysis module 115 analyzes the captured images to determine one or more optical parameters (e.g., IPD, prescription information) of the eyewear device 132. The analysis module 115 may provide the determined information to the user via a user interface of the user device 110. The analysis module 115 determines one or more optical parameters of the eyewear device 132 based on the captured one or more images of the test pattern 122 as seen through the eyewear device 132. For example, the analysis module 115 applies a Fourier Transform to the one or more captured images. The analysis module 115 determines a distance between features the Fourier Transform of a reference image (e.g., test pattern 122 or a calibration image of the test pattern 122 not through the lens 130) and compares it to a distance between corresponding features of a Fourier Transform of the captured image of the test pattern 122 through the lens 130. The analysis module 115 determines an optical parameter of the eyewear device 132. In one embodiment, the analysis module 115 computes a ratio of the determined distances of the Fourier Transform of the reference image and the Fourier Transform of the captured image to determine an optical parameter of the eyewear device 132. In one embodiment, the optical parameter of the eyewear device 132 is an optical power of a lens 130 of the eyewear device. The optical power of the lens 130 may be based on the first distance separating the display surface 121 and the lens 130 and the second distance separating the lens 130 and the imaging device 112. In one embodiment, the optical power of the lens is a spherical correction. In another embodiment, the optical power of the lens is a cylinder correction and the one or more optical parameters of the eyewear device 132 further comprise an axis. In one or more embodiments, the analysis module 115 could be performed by some other element. For example, the analysis module 115 may not be included in the user device 110 and could be a module on a remote server in the network 140.

Figure 2:
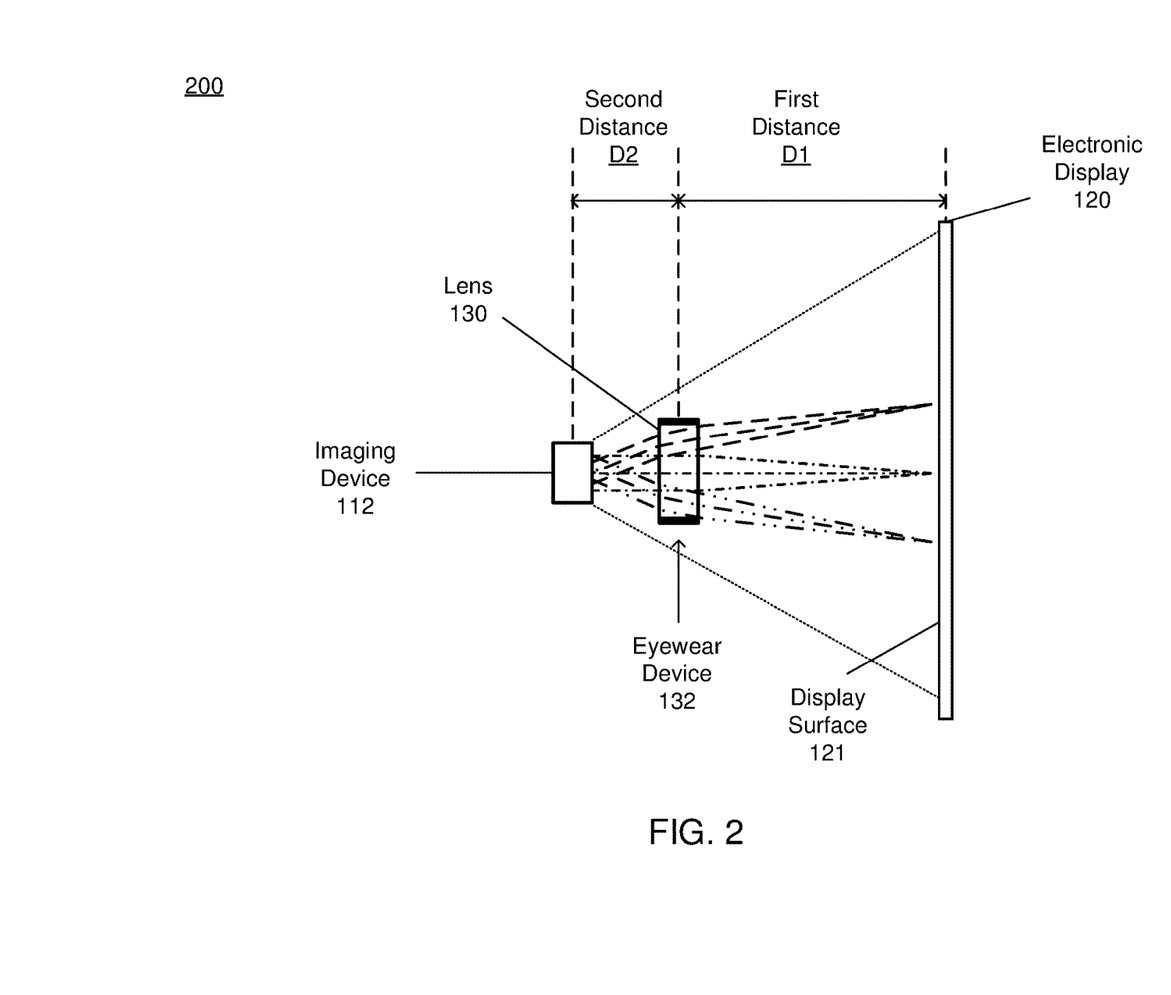
FIG. 2 is a cross section of the example configuration of an imaging device, eyewear device, and electronic display for capturing one or more images including an eyewear device, in accordance with one or more embodiments.

FIG. 2 is a cross section 200 of the example configuration of an imaging device 112, eyewear device 132, and electronic display 120 for capturing one or more images including an the eyewear device 132, in accordance with one or more embodiments.

In the cross section 200, the lens 130 is a first distance D1 from the display surface 121, and the imaging device 112 is a second distance D2 from the lens 130. In one embodiment, the first distance D1 and the second distance D2 are included in the imaging instructions from the controller 114. For example, the first distance D1 and the second distance D2 may be provided to the user via the user device 110 and the user may place a lens 130 at the first distance D1 from the display surface 121 and the imaging device 112 a second distance D2 from the lens 130 of the eyewear device 132. The user may use a ruler to determine these distances and place the imaging device 112, lens 130, and the display surface 121 at the appropriate distances. Alternatively, the user may use a mechanical fixture that holds the user device 110 (including the imaging device 112), lens 130, and display surface 121 at the appropriate distances. In one embodiment, the user device 110 may include a depth camera assembly for measuring the first distance D1 and the second distance D2 when the imaging device 112 captures a test image. The depth camera assembly may include one or more imaging devices and one or more light sources for determining a depth using any one or combination of the following: stereo vision, structured light, and time of flight technique. In one embodiment, the controller 114 uses information from the depth camera assembly to verify the first distance D1 or the second distance D2 before instructing the imaging device 112 to capture a test image. For example, the controller 114 may instruct the user to place the imaging device 112 a distance D1+D2 away from the display surface 121, and instruct the user to move the lens 130 of the eyewear device 132 along an axis perpendicular to a surface of the imaging device 112 and the display surface 121. Once the controller 114 determines via the depth camera assembly that the display surface 121 is a first distance D1 from the lens 130 and/or the lens 130 is a second distance D2 from the imaging device 112, the controller 114 may instruct the imaging device 112 to capture an image of the eyewear device 132. In a different embodiment, one distance may be fixed (e.g., D1 or D2) and another distance (e.g., D2 or D1) may be determined by the depth camera assembly. In another example, the second distance D2 is fixed and may be provided by the controller 114. A user may move the imaging device 112 towards the lens 130. The controller 114 may use the depth camera assembly to determine when the imaging device 112 is at the second distance D2 from the lens 130. When the appropriate distance is reached, the controller 114 instructs the imaging device 112 to capture an image of the test pattern 122 displayed on the display surface 121 through the lens 130 and the test pattern 122 not through the lens 130 (e.g., region between two lenses 130 of an eyewear device 132). When the image is captured, the controller 114 also instructs the depth camera assembly to determine or provide information to determine the first distance D1 between the lens and the display surface 121. The user device 110 may then notify the user that the image is captured. In one embodiment, the first distance D1 and the second distance D2 is not predetermined (e.g., provided by the controller 114) and the depth camera assembly determines or provides information for determining the first distance D1 and the second distance D2 to the controller 114 when a test image is captured by the imaging device 112. The controller 114 may use a frame of an eyewear device 132 to estimate the distance of the lens 130 to the eyewear device 132.

The focal length F of the lens 130 can be determined by using the following first order approximation formula as shown below in equation 1

$$F = \frac{D1 \times D2 \times M}{(D1 + D2) \times (M - 1)} \quad (1)$$

where M is an image magnification that can be determined from analysis of a captured image of the test pattern 122 through a lens 130 of the eyewear device 132 and the test pattern that is not through the lens 130, as described further in relation to FIGS. 3A-3C. In eyewear device 132, the lens 130 may include astigmatism correction such that a focal length corresponding to a region along an axis on the surface of the lens 130 in a 0, 45, and 90 degrees direction can differ. In one embodiment, four different magnification factors can be determined at 0, 90, −45, and 45 degree directions. The four different focal lengths can be calculated, and an average of the four focal lengths may be used for the correction.

FIG. 3A is an example test image 300 that includes an eyewear device 132, in accordance with one or more embodiments. A test image is an image captured from the imaging device 112. The test image 300 shown in FIG. 3A includes the eyewear device 132 and two lenses 130 (e.g., lens 130a and 130b) of the eyewear device 132. The test image 300 includes the eyewear device 132, a first region 301 (e.g., first region 301a and 301b) of a test pattern 122 through a lens 130 of the eyewear device 132 and a second region 302 of a test pattern 122 that is not through the lens 130 of the eyewear device 132. The second region 302 includes the test pattern 122 captured in an adjacent region that is not through the lens 130 of eyewear device 132 (e.g., lens and frame of the eyewear device 132). For example, an adjacent region may be an area in between both lenses of the eyewear device 132 and outside of the frame of the eyewear device 132 as shown in FIG. 3A as second region 302. The adjacent region may be an area outside a lens and frame of an eyewear device 132 such as a region to the top, bottom, or sides outside the eyewear device 132. There is a difference in magnification when viewing the test pattern 122 through the lens as shown in the first region 301 and viewing the test pattern 122 outside of the lens as shown in the second region 302. In this example, the magnification of the test pattern 122 through the lens as shown in the first region 301 appears to be smaller than the magnification outside of the lens 130 as shown in the second region 302.

FIG. 3B is a portion 320 of the test image that includes a lens 130a of an eyewear device 132 of FIG. 3A, in accordance with one or more embodiments. The portion 320 includes a single lens 130 of the eyewear device 132. The test pattern 122 is shown through the lens 130a of the eyewear device 132 as shown in the first region 301a and also not through the lens 130 of the eyewear device 132 as shown in the second region 302.

FIG. 3C is an example Fourier Transform 340 of a region of the portion 320 of the test image 300 that includes the lens 130a of the eyewear device 132 of FIG. 3B, in accordance with one or more embodiments. The analysis module 115 applies a Fourier Transform to a region of the portion 320 of the test image 300. The result is the Fourier Transform 340 which includes a series of peaks or features f1, f1' to f8, f8'. The features f1 and f1', f3 and f3', f5 and f5', and f7 and f7' correspond to frequencies of the portion 320 of the test image 300 in a second region 302 where there is no lens 130. The peak pairs f2 and f2', f4 and f4', f6 and f6', f8 and f8' correspond to frequencies of the portion 320 of the test image 300 in a first region 301a through a lens 130. The analysis module 115 identifies multiple pairs of features and maps them to corresponding regions such as first region 301a and second region 302. For example, the analysis module 115 identifies a first pair of features f1 and f1', a second pair of features f2 and f2' along a same axis. The features f1 and f1' along the fx axis at (fx+1, fy0) and (fx−1, fy0) corresponds to a frequency of the test pattern 122 in a horizontal direction of the second region 302. Corresponding features f2 and f2' along the fx axis at (fx+2, fy0) and (fx−2, fy0) correspond to a frequency of the test pattern 122 in a horizontal direction in a first region 301a. The analysis module 115 determines a distance x2 between the f1 and the feature f1' of the Fourier Transform 340 which is the spacing between fx+1 and fx−1. The analysis module 115 determines a distance x1 between the corresponding feature f2 and the corresponding feature f2' of the Fourier Transform 340 which is the spacing between fx+2 and fx−2. The image magnification M at zero degrees (e.g., magnification of the lens region along a horizontal axis on the surface of the lens 130) can be calculated as the ratio between x1 and x2. Other magnification factors can be calculated by looking at the peak pairs in the other directions. For example, a feature f3 and a feature f3' along the fy axis at (fx0, fy+1) and (fx0, fy−1) corresponds to a frequency of the test image 122 in a vertical direction of the second region 302. A corresponding feature f4 and corresponding feature f4' along the fy axis at (fx0, fy+2) and (fx0, fy−2) corresponds to a frequency of the test image 122 in a vertical direction of the first region 301a. Similarly, the analysis module 115 can determine a distance y2 between the feature f3 and feature f3' which is the spacing between fy−1 and fy+1 and a distance y1 between the corresponding feature f4 and corresponding feature f4' which is the spacing between fy−2 and fy+2. The analysis module 115 can compute an image magnification at ninety degrees as the ratio between y1 and y2. Similarly, the analysis module 115 can determine an image magnification at 45 degrees from features f5 and f5' and corresponding features f6 and f6' as well as an image magnification at −45 degrees from the features f7 and f7' and corresponding features f8 and f8'.

The analysis module 115 determines an optical parameter of the eyewear device 132. In one embodiment, the analysis module 115 computes a ratio of the distance x1 and distance x2 to determine an optical parameter of the eyewear device 132. In one embodiment, the optical parameter of the eyewear device 132 is an optical power (e.g., magnification M) of the lens 130 of the eyewear device 132. Once the magnification M is determined, the focal length of the lens can be determined by using the previously described equation 1. Thus, the optical power of the lens is based on the first distance D1 separating the display surface 121 and the lens 130 and the second distance D2 separating the lens 130 and the imaging device 112. In one embodiment, the optical power of the lens is a spherical correction. For example, in determining the optical parameter of the eyewear device 132, the analysis module 115 may compute a magnification in a horizontal direction and a magnification in a vertical direction from a Fourier Transform of a portion of a test image, and these magnifications may be similar or the same. In another embodiment, the optical power of the lens is a cylinder correction and the one or more optical parameters of the eyewear device 132 further comprise an axis. Additionally, more than one axis may be included. A cylinder correction indicates that there is a difference in magnification power between different axes. The axis may be a number between 0 and 180 degrees. For example, the analysis module 115 may determine one or more axes based on a comparison of features in the Fourier Transform of the portion of the test image. The analysis module 115 may determine a magnification in a horizontal direction is different from a magnification in a vertical direction. The analysis module 115 may assign a first number as a spherical power of a correction along a first axis (e.g., horizontal axis) and a second number as a cylinder power for a cylinder correction along a second axis (e.g., vertical axis).

Figure 4:
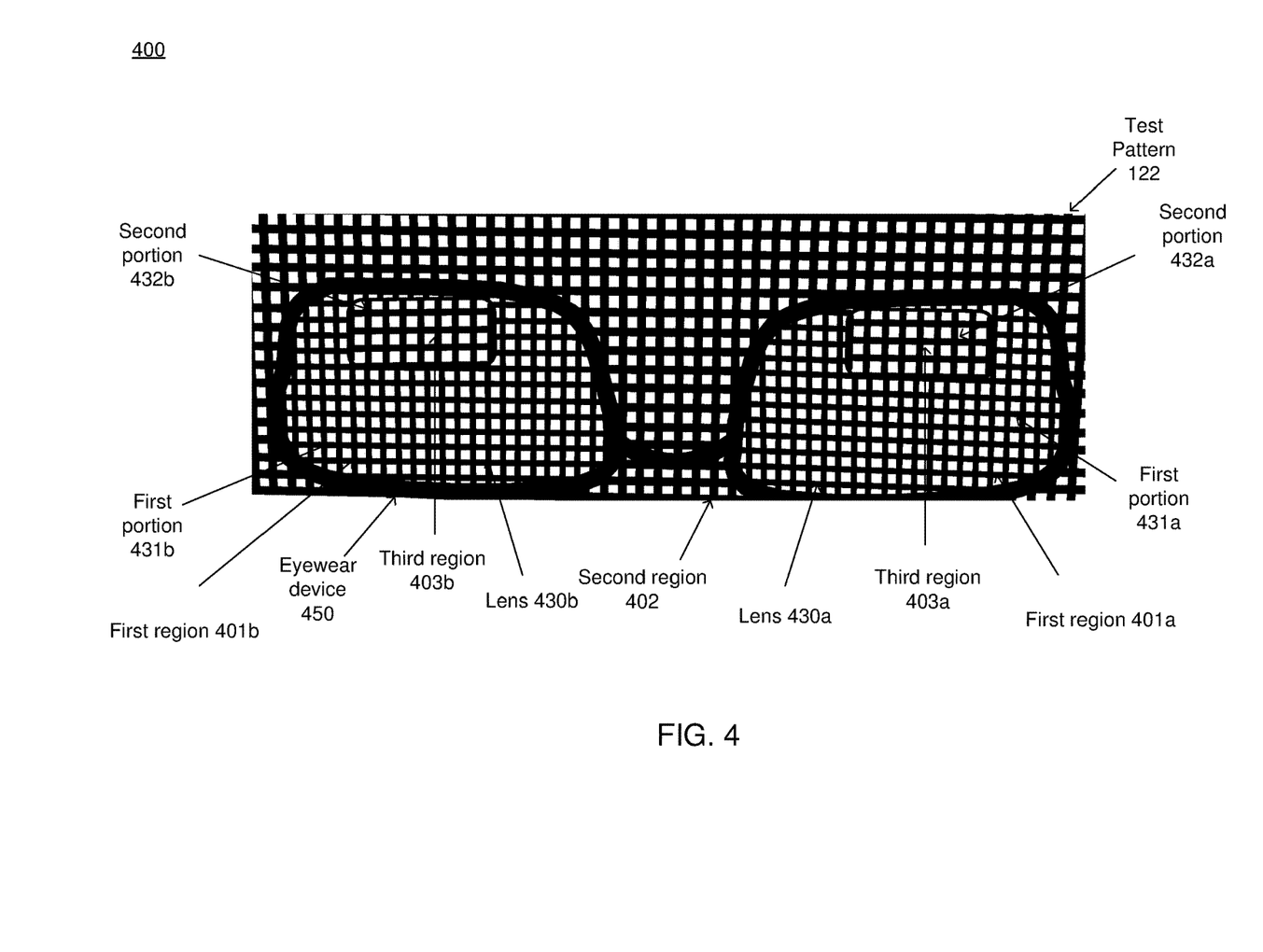
FIG. 4 is an example test image that includes a bifocal eyewear device, in accordance with one or more embodiments.

FIG. 4 is an example test image 400 that includes a bifocal eyewear device 450, in accordance with one or more embodiments. In the example test image 400 of FIG. 4, a test pattern 122 is captured in a first region 401 (e.g., first region 401a and 401b), a second region 402, and a third region 403 (e.g., third region 403a and 403b). The first region 401 is the test pattern 122 captured through a first portion 431 (e.g., first portion 431a and 431b) of the lens 430 of the eyewear device 450. The second region 402 is the test pattern 122 captured in an adjacent region that is not through the lens 430 of eyewear device 450 (e.g., lens and frame of the eyewear device 450). The second region 402 and adjacent region is similar to the second region 302 and adjacent region previously described with respect to FIG. 3A. The third region 403 is the test pattern 122 captured through a second portion 432 (e.g., second portion 432a and 432b) of the lens 430 of the eyewear device 450. The second portion 432 of the lens 430 has a different optical power than the first portion 431 of the lens 430.

Non-circularly symmetric lenses are measured differently than circularly symmetric lenses. Bifocal and transition lenses are examples of non-circularly symmetric lenses with different zones of optical power. For a bifocal lens, the analysis module 115 may perform a Fourier Transform on a portion of a test image 400 and select pairs of peaks independently for each optical zone of magnification. For example, the Fourier Transform may be similar to an example Fourier Transform 340 of a region of the portion 320 of the test image 300 except there may be additional peak pairs in a horizontal and vertical direction corresponding to frequencies of the test pattern 122 in the third region 403a. A distance (e.g., x3) may be computed for the distance between peak pairs corresponding to frequencies in the third region 403a and the analysis module 115 may compute a ratio of the distance x1 (e.g., corresponding to frequencies of the test pattern 122 in the second region 402) and distance x3 to compute an optical power of the second portion 432a of the lens 430a. The analysis module 115 may compute the optical power of the second portion 432a of the lens 430a relative to an optical power of the first portion 431a of the lens 430a and the analysis module 115 may determine an optical parameter of the eyewear 450 such as an add parameter to indicate additional refractive power to be added to the optical power of the first portion 431a of the lens 430a. For a progressive lens with astigmatic correction where the focal length in one axis is different than the focal length in another axis, the analysis module 115 may select pairs of peaks of a corresponding Fourier Transform on a portion of a test image including the progressive lens in a same optical zone for each optical zone of the progressive lens. Similarly to the case of a bifocal lens, the analysis module 115 may identify pairs of peaks in a horizontal direction, a vertical direction, or other direction, and compute ratios of distances between the pairs of peaks to compute an optical power of a corresponding optical zone.

Additionally, image distortion typically increases away from the center of the lens. For strong lenses (8 diopters) versus a weak lens (2 diopters), the strong lens has a greater variation outside the central portion of the lens. For strong prescription lenses, an optical power of the lens in the central portion tends to be more accurate than a peripheral portion of the lens.

Figure 5:
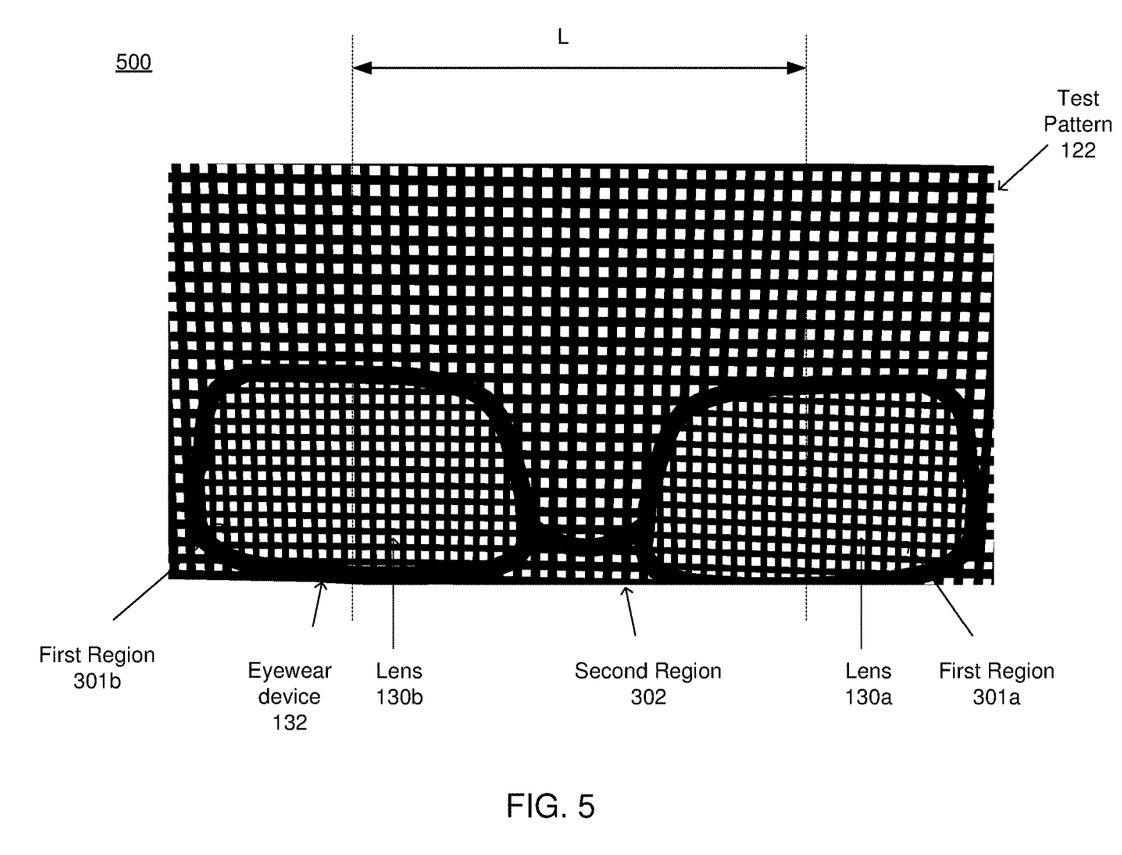
FIG. 5 is an example test image that includes an eyewear device for determining an IPD of a user of the eyewear device, in accordance with one or more embodiments.

FIG. 5 is an example test image 500 that includes an eyewear device 132 for determining an IPD of a user of the eyewear device 132, in accordance with one or more embodiments. The example test image 500 is the same as the example test image 300 except a length L are indicated on the test image 500. The length L indicates a distance corresponding to the IPD on the test image 500. The length L of a distance on the display surface 121 can be estimated by using the spacing of features of the test pattern 122.

Figure 6:
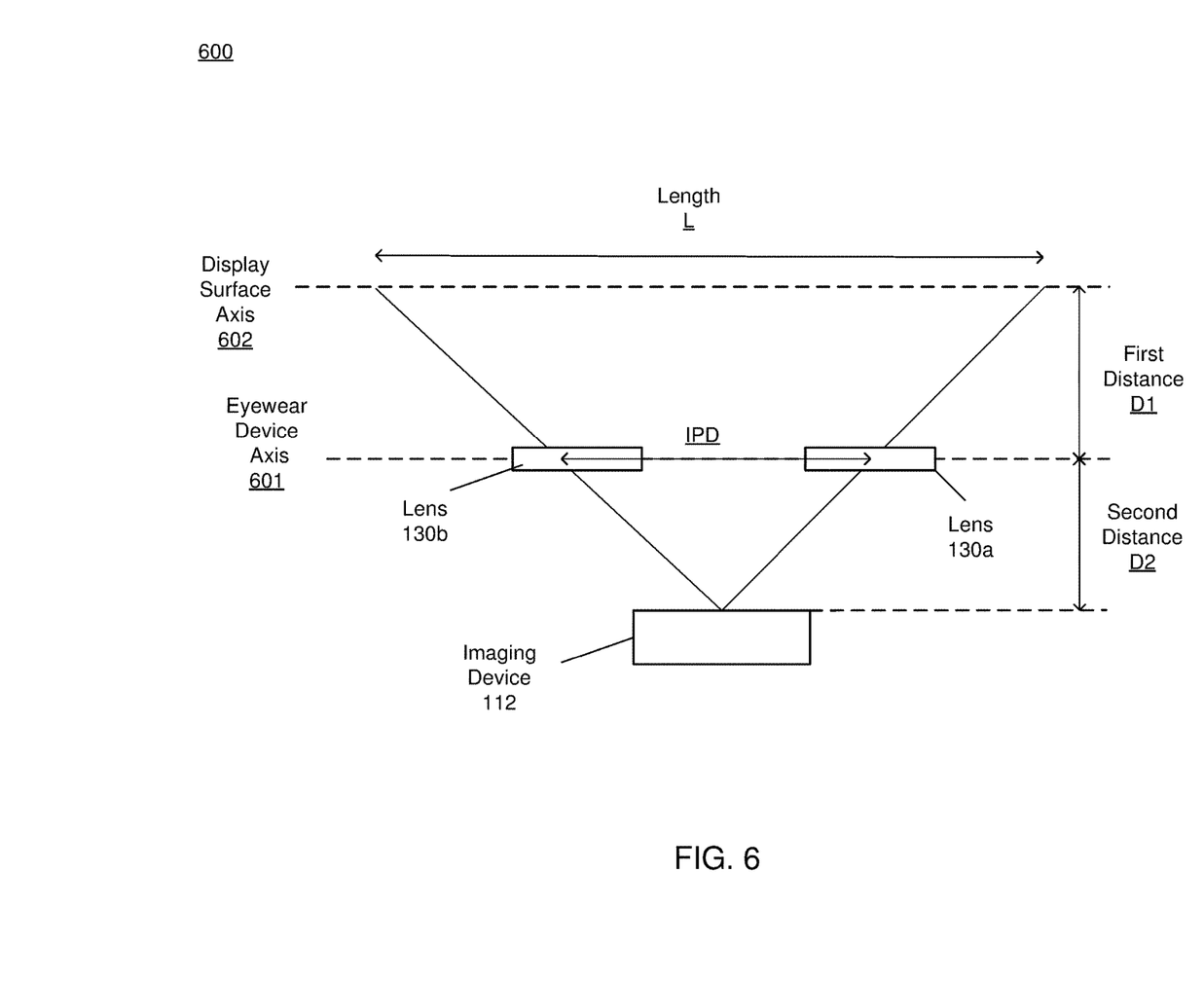
FIG. 6 is a plan view of the imaging device, eyewear device/lens axis, and a display surface axis for determining an IPD of a user of the eyewear device, in accordance with one or more embodiments.

The analysis module 115 can determine the IPD based on the length L and a first distance D1 and a second distance D2, which is described in more detail with respect to FIG. 6. The analysis module 115 can determine the IPD from the relative position of a test pattern 122 as shown through the lens 130 in first region 301 and a test pattern 122 that is not shown through the lens 130 in a second region 302. The first region 301 includes a first region 301a corresponding to the test pattern 122 shown through one lens of the eyewear device 132, and a first region 301b corresponding to the test pattern 122 shown through another lens of the eyewear device 132.

FIG. 6 is a plan view 600 of the imaging device, eyewear device/lens axis, and display surface axis for determining an IPD of a user of the eyewear device, in accordance with one or more embodiments. The plan view 600 includes the imaging device 112, the lenses 130a and 130b, an eyewear device axis 601, and a display surface axis 602. The lenses 130a and 130b are positioned along the eyewear device axis 601. A display surface 121 (not shown) is positioned along the display surface axis 602. The first distance D1 is a distance of the lens 130a or lens 130b to the display surface 121. The second distance D2 is a distance from the imaging device 112 to the lens 130a or the lens 130b. A length L is a distance corresponding to the IPD on the display surface 121. The IPD can be determined from the following equation 2.

$$IPD = \frac{L \times D2}{D1 + D2} \quad (2)$$

For example, the analysis module 115 can determine a length L by marking a distance L corresponding to the IPD of the eyewear device shown in FIG. 5. For example, to mark the distance L, the analysis module 115 can determine a shape (e.g., boundary) of the first region 301a and the first region 301b in the test image 500 via edge detection of a frame of the eyewear device 132 or analysis of spatial frequency of the test pattern 122 in different portions of the image 500. Once the shape of the first regions 301a and 301b are determined, the analysis module 115 can then determine a geometric center of the first region 301a and a geometric center of the first region 301b. The distance L is marked by a line drawn from the geometric centers of the first region 301 and the first region 301b. The distance L on the display surface 121 can be estimated by the spacing of features in a test pattern (e.g., grid spacing). For example, in the test image 500, the analysis module 115 can estimate the distance L by counting a number of features of the test pattern 122 that are included in the distance L and multiplying the number of features by the known spacing of the features. The IPD can be determined by substituting the determined L and known first distance D1 and second distance D2 in equation 2.

Figure 7:
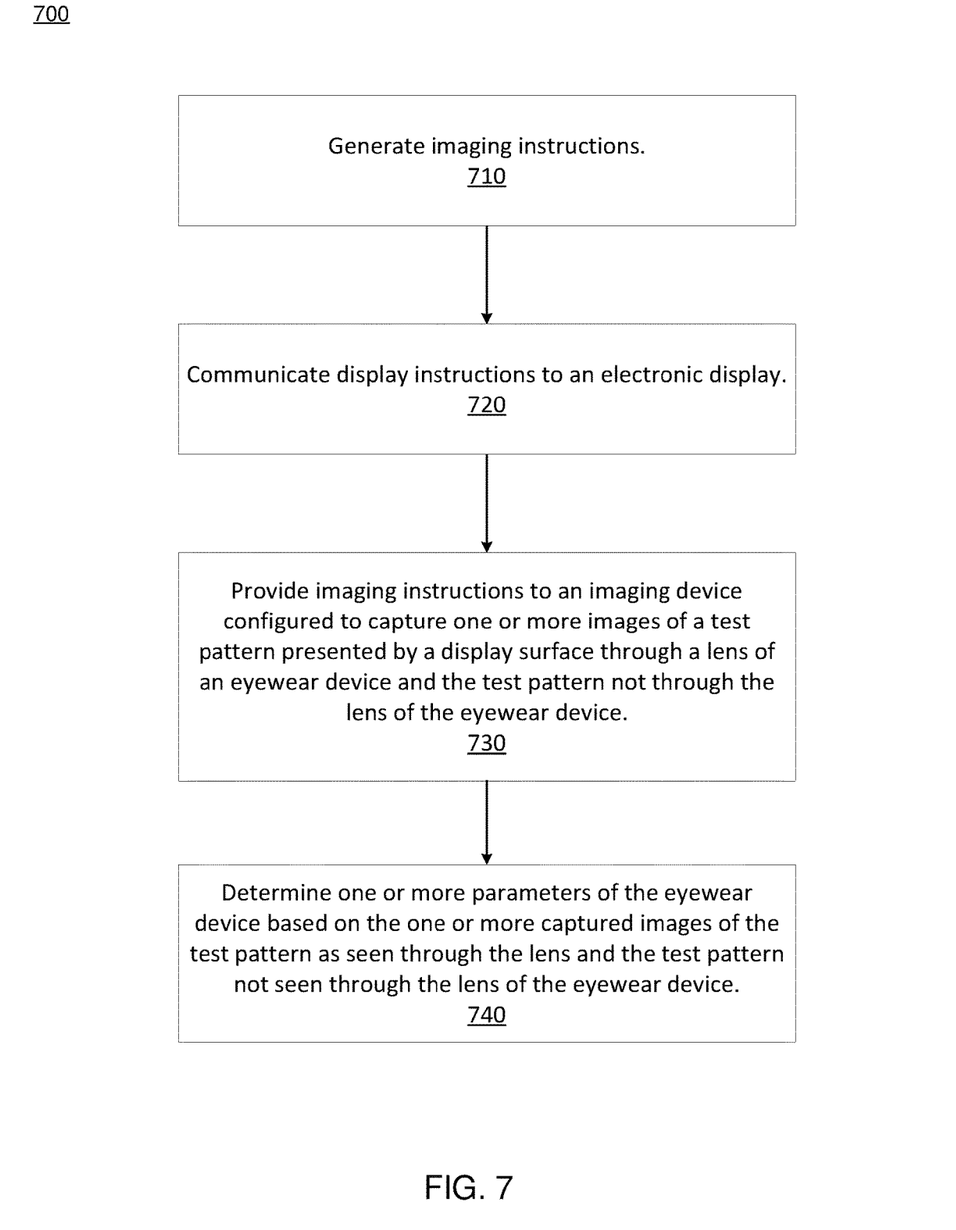
FIG. 7 is a process flow for determining one or more optical parameters of an eyewear device, in accordance with one or more embodiments.

FIG. 7 is a process flow 700 for determining one or more optical parameters of an eyewear device, in accordance with one or more embodiments. The process 700 of FIG. 7 may be performed by a user device 110 (e.g., via an optical measurement application 111). Other entities may perform some or all of the steps of the process in other embodiments. For example, a server may perform some of the steps of the process. Likewise, embodiments may include different and/ or additional steps, or perform the steps in different orders.

The user device 110 generates 710 imaging instructions. The imaging instructions may include instructions for a user to place a lens between the imaging device 112 and the display surface 121. The imaging instructions include instructions for the imaging device 112 for capturing one or more images of a test pattern on the display surface 121 through a lens 130 and the test pattern 122 on the display surface 121 not through the lens 130.

The user device 110 communicates 720 display instructions to an electronic display 120. The user device 110 may directly provide display instructions to the electronic display 120 via the network 140. In one embodiment, the user device 110 may ping a remote server to provide display instructions to the electronic display 120 via the network 140. In another embodiment, the user device 110 may display instructions for a user to download display instructions at a remote server. The user may download the display instructions via a corresponding processor of an electronic display 120 from the remote server. In one embodiment, an electronic display 120 and network 140 may not be included in the system and the step 720 may be omitted.

The user device 110 provides 730 imaging instructions to an imaging device 112. The imaging instructions may be directions to the user to activate the imaging device to capture an image once the user has proper placement of the lens between the test pattern on the display device and imaging device. The imaging instructions may be directions for the imaging device to capture an image once the user has proper placement of the lens relative to the test pattern on the display device and/or the imaging device, once features of a test pattern are in focus, features of a test pattern or the entire test pattern is in a field of view of the imaging device, whether there is appropriate contrast or lighting conditions for capturing the image, or a combination thereof. The imaging device 112 captures one or more images of a test pattern 122 presented by an display surface 121 through a lens 130 of eyewear device and the test pattern 122 presented by an display surface 121 not through a lens 130 of the eyewear device.

The user device 110 determines 740 one or more optical parameters of the eyewear device 132 based on the one or more captured images of the test pattern as seen through the lens 130 and not seen through the lens 130 of the eyewear device 132. The user device 110 may determine an optical power of the lens 130. The user device may apply a Fourier Transform to the one or more captured images. The optical measurement application 111 determines a distance between features the Fourier Transform of a reference image (e.g., test pattern 122 or a calibration image of the test pattern 122 not through the lens 130) and compares it to a distance between corresponding features of a Fourier Transform of the captured image of the test pattern 122 through the lens 130. The user device 110 determines an optical parameter of the eyewear device 132. In one embodiment, the user device 110 computes a ratio of the determined distances of the Fourier Transform of the reference image and the Fourier Transform of the captured image to determine an optical parameter of the eyewear device 132. In one embodiment, the optical parameter of the eyewear device 132 is an optical power of the lens 130 of the eyewear device 132. In one embodiment, the optical parameter of the eyewear device 132 is an IPD. The IPD is determined based on estimated a determined length L, first distance D1, and second distance D2.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A device comprising:
   an imaging device configured to capture one or more images of a test pattern presented by a display surface through a lens of an eyewear device and the test pattern not through the lens of the eyewear device in accordance with imagining instructions; and
   a controller configured to:
   generate imaging instructions and provide the imaging instructions to the imaging device, and
   determine one or more optical parameters of the eyewear device based on the captured one or more images of the test pattern as seen through the lens and the test pattern not seen through the lens, the one or more optical parameters of the eyewear device including an optical power of the lens.

2. The device of claim 1, wherein the controller is configured to determine the optical parameters of the eyewear device by applying a Fourier transform to the one or more captured image and computing a ratio of a distance between features on the Fourier transform of the one or more captured image to a corresponding distance between features on the Fourier transform of the test pattern.

3. The device of claim 1, wherein the controller is further configured to communicate display instructions to an electronic display and provide the display instructions comprising the test pattern to the electronic display, wherein a surface of the electronic display is the display surface.

4. The device of claim 1, wherein the controller instructs a user to place the lens a first distance from the display surface and the imaging device a second distance from the lens, and the controller is configured to determine the optical power of the lens based on the first distance and the second distance.

5. The device of claim 1, wherein the display surface is a surface of an electronic display selected from a group consisting of: a laptop, a desktop, and a smart television and wherein the device is a device selected from a group consisting of: a mobile phone controlling the imaging device, a tablet controlling the imaging device, and a laptop controlling the imaging device.

6. The device of claim 1, wherein the one or more optical parameters of the eyewear device includes an inter-pupillary distance of a user of the eyewear device.

7. The device of claim 1, wherein the one or more images is a series of images and the imaging instructions include instructions for capturing the series of images as a user moves the device relative to the lens.

8. The device of claim 1, wherein the imaging instructions include instructions for the imaging device to capture the one or more images responsive to a user input.

9. The device of claim 1, wherein the optical power of the lens is a spherical correction.

10. The device of claim 1, wherein the optical power of the lens is a cylinder correction and the one or more optical parameters of the eyewear device further comprise an axis.

11. A non-transitory computer-readable storage medium storing executable computer program instructions, the computer program instructions comprising instructions for:
generating imaging instructions;
providing imaging instructions to an imaging device configured to capture one or more images of a test pattern presented by a display surface through a lens of an eyewear device and the test pattern not through the lens of the eyewear device; and
determining one or more optical parameters of the eyewear device based on the one or more captured images of the test pattern as seen through the lens and the test pattern not seen through the lens, the one or more optical parameters of the eyewear device including an optical power of the lens.

12. The computer readable medium of claim 11, wherein the instructions for determining the one or more optical parameters of the eyewear device further comprise instructions for applying a Fourier transform to the captured image and computing a ratio of a distance between features on the Fourier transform of the captured image to a corresponding distance between features on the Fourier transform of the test pattern.

13. The computer readable medium of claim 11, further comprising computer program instructions comprising instructions for communicating display instructions to an electronic display and providing the display instructions comprising the test pattern to the electronic display, wherein a surface of the electronic display is the display surface.

14. The computer readable medium of claim 11, further comprising computer program instructions comprising instructions for instructing a user to place the lens a first distance from the display surface and the imaging device a second distance from the lens, and the instructions for determining the one or more optical parameters of the eyewear device is based on the first distance and the second distance.

15. The computer readable medium of claim 11, wherein the display surface is a surface of an electronic display selected from a group consisting of: a laptop, a desktop, and a smart television, and wherein is a device comprising the imaging device is selected from a group consisting of: a mobile phone controlling the imaging device, a tablet controlling the imaging device, and a laptop controlling the imaging device.

16. The computer readable medium of claim 11, wherein the one or more optical parameters of the eyewear device includes an inter-pupillary distance of a user of the eyewear device.

17. The computer readable medium of claim 11, wherein the one or more images is a series of images and the imaging instructions include instructions for capturing the series of images as a user moves a device comprising the imaging device relative to the lens.

18. The computer readable medium of claim 11, wherein the imaging instructions include instructions for the imaging device to capture the one or more images responsive to a user input.

19. The computer readable medium of claim 11, wherein the optical power of the lens is a spherical correction.

20. The computer readable medium of claim 11, wherein the optical power of the lens is a cylinder correction and the one or more optical parameters of the eyewear device further comprise an axis.

* * * * *

UNITED STATES PATENT AND TRADEMARK OFFICE
CERTIFICATE OF CORRECTION

PATENT NO. : 10,321,820 B1
APPLICATION NO. : 15/850815
DATED : June 18, 2019
INVENTOR(S) : Jacques Gollier and Yusufu Njoni Bamaxam Sulai Page 1 of 1

It is certified that error appears in the above-identified patent and that said Letters Patent is hereby corrected as shown below:

In the Claims

Column 15, Line 33, Claim 12, after "The" delete "computer readable" and insert -- computer-readable --.
Column 15, Line 41, Claim 13, after "The" delete "computer readable" and insert -- computer-readable --.
Column 16, Line 5, Claim 14, after "The" delete "computer readable" and insert -- computer-readable --.
Column 16, Line 13, Claim 15, after "The" delete "computer readable" and insert -- computer-readable --.
Column 16, Line 16, Claim 15, after "wherein" delete "is".
Column 16, Line 22, Claim 16, after "The" delete "computer readable" and insert -- computer-readable --.
Column 16, Line 26, Claim 17, after "The" delete "computer readable" and insert -- computer-readable --.
Column 16, Line 31, Claim 18, after "The" delete "computer readable" and insert -- computer-readable --.
Column 16, Line 35, Claim 19, after "The" delete "computer readable" and insert -- computer-readable --.
Column 16, Line 37, Claim 20, after "The" delete "computer readable" and insert -- computer-readable --.

Signed and Sealed this
Third Day of December, 2019

Andrei Iancu
*Director of the United States Patent and Trademark Office*